United States Patent [19] [11] Patent Number: 5,976,137
Mayer [45] Date of Patent: Nov. 2, 1999

[54] INTRAMEDULLARY ROD SYSTEM USING MODULAR CUTTING SPLINES

[76] Inventor: Paul W. Mayer, 6290 SW. 92nd St., Miami, Fla. 33156

[21] Appl. No.: 08/979,930

[22] Filed: Nov. 26, 1997

Related U.S. Application Data

[60] Provisional application No. 60/031,872, Nov. 27, 1996.

[51] Int. Cl.[6] .................................................. A61B 17/56
[52] U.S. Cl. ................... 606/62; 606/63; 606/64; 606/60; 606/72; 606/80; 606/85; 606/79
[58] Field of Search ................. 606/62, 63, 64, 606/60, 72, 80, 85, 79

[56] References Cited

U.S. PATENT DOCUMENTS

| | | |
|---|---|---|
| 4,473,070 | 9/1984 | Matthews et al. . |
| 4,678,471 | 7/1987 | Noble et al. . |
| 4,784,127 | 11/1988 | Mattheck et al. . |
| 4,805,607 | 2/1989 | Engelhardt et al. . |
| 5,034,013 | 7/1991 | Kyle et al. . |
| 5,116,335 | 5/1992 | Hannon et al. . |
| 5,171,277 | 12/1992 | Roger . |
| 5,281,225 | 1/1994 | Vicenzi ...................................... 606/62 |
| 5,433,718 | 7/1995 | Brinker . |
| 5,458,600 | 10/1995 | Stapert et al. . |
| 5,562,665 | 10/1996 | Young . |
| 5,603,715 | 2/1997 | Kessler ...................................... 606/63 |
| 5,653,712 | 8/1997 | Stern . |
| 5,810,820 | 9/1998 | Santori et al. ............................ 606/63 |

FOREIGN PATENT DOCUMENTS 3209403 9/1983 Germany .

*Primary Examiner*—Michael Buiz
*Assistant Examiner*—(Jackie) Tan-Uyen T. Ho
*Attorney, Agent, or Firm*—Browdy and Neimark

[57] ABSTRACT

An intramedullary rod or nail for aligning a fractured long bone has a rod (100) that is inserted into the bone, with two longitudinal slots (120) into which cutting splines (200) are slid. The splines have cutting teeth (250) for cutting grooves into the bone as the splines slide along the slot. The cutting edges are substantially transverse to the length of the splines and rod. The tooth top surfaces (252) are disposed at gradually increasing radial heights. Recesses (251) between the cutting teeth store bone shavings to prevent jamming. The bone segments are held against bending, rotation, and lateral displacement because the splines are firmly engaged in the grooves they have cut. A blank spline without teeth may replace the cutting spline.

19 Claims, 4 Drawing Sheets

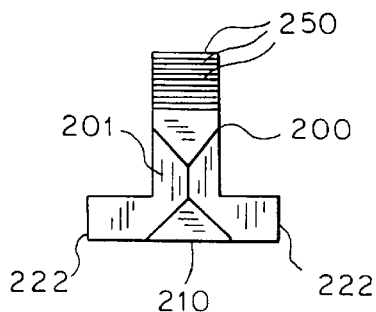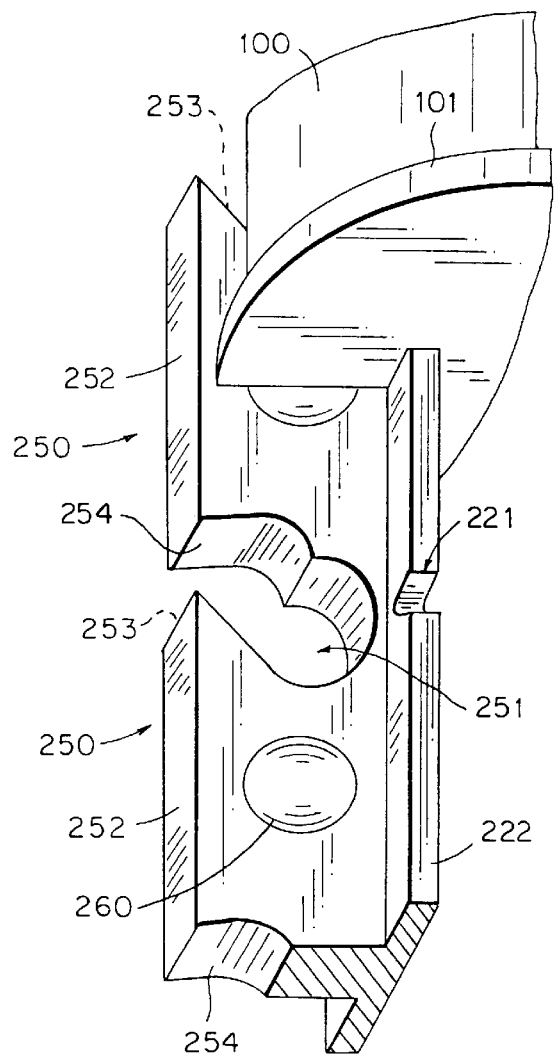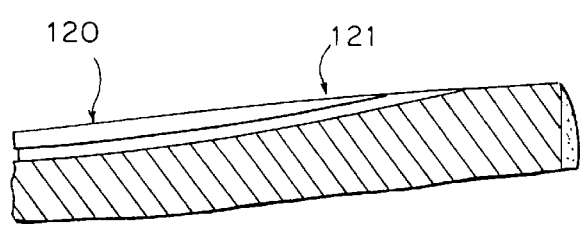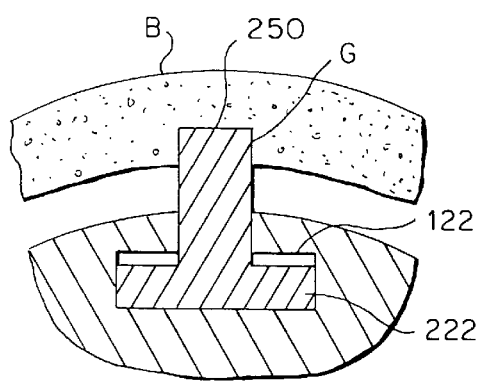

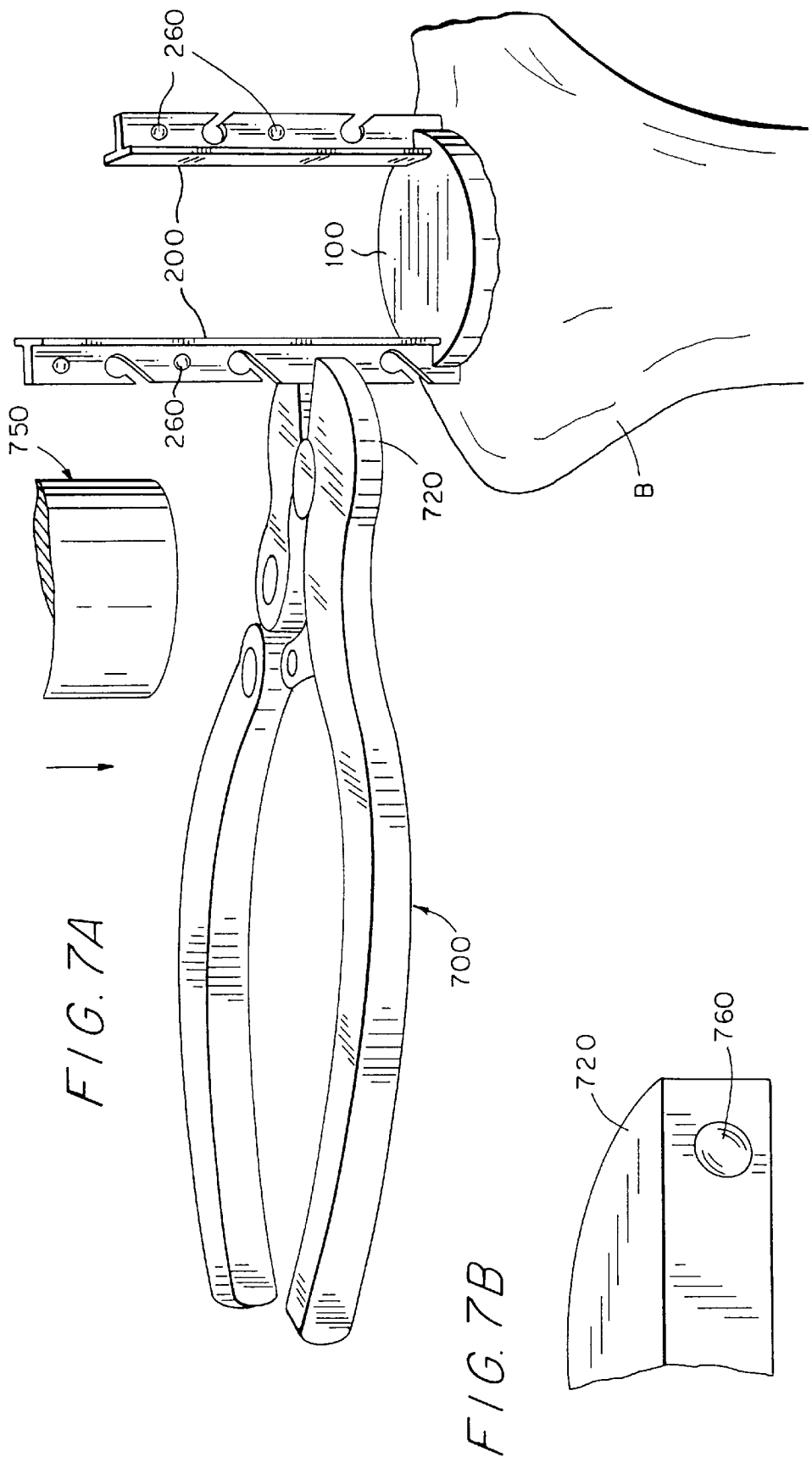

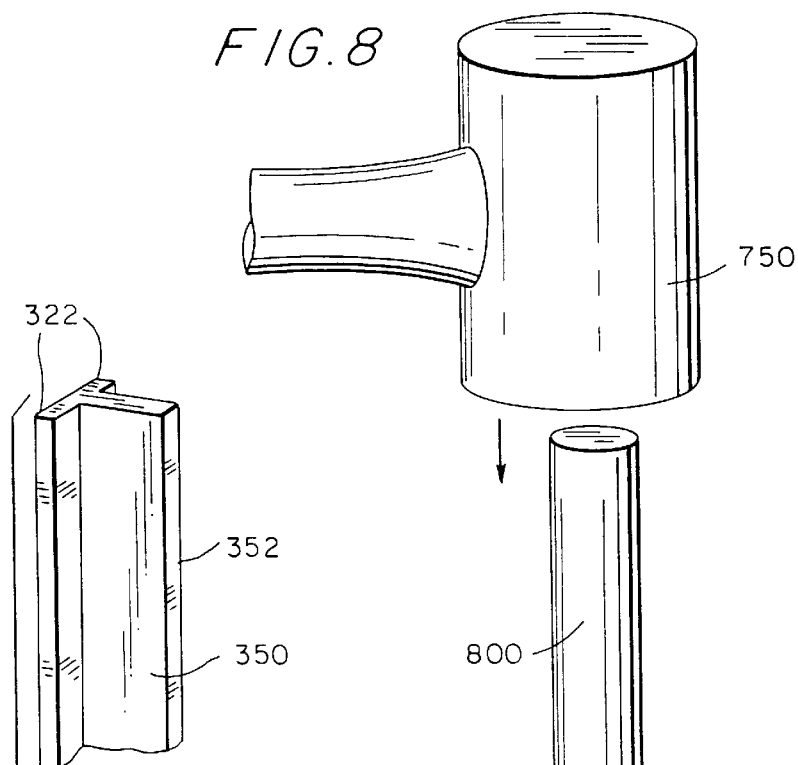
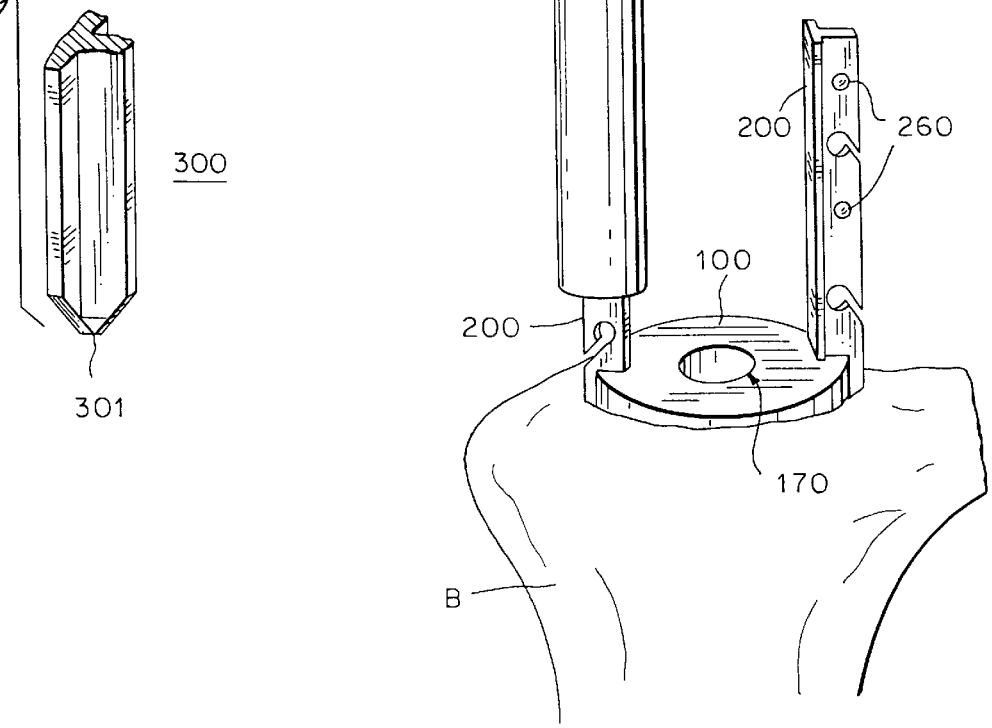

INTRAMEDULLARY ROD SYSTEM USING MODULAR CUTTING SPLINES

CROSS-REFERENCE TO RELATED APPLICATION

This application claims the benefit of U.S. Provisional Application No. 60/031,872 filed on Nov. 27, 1996, the entire contents of which are hereby incorporated herein by reference.

FIELD OF THE INVENTION

The present invention relates to an intramedullary rod (or "nail") surgically inserted into a long bone, especially the femur or tibia, and more particularly to such a rod containing removable cutting splines for anchoring the rod into the bone.

REVIEW OF THE RELATED TECHNOLOGY

When a long bone such as the femur or tibia is fractured, the bone must be set. This has been accomplished by bolting or screwing the broken segments with transverse screws to a holed plate laid alongside the bone.

Such a plate system has several drawbacks, notably the difficulty of achieving the correct rotational alignment of the broken segments while simultaneously aligning the segments linearly and keeping the fractured ends together. The bone segments must be carefully maintained in precise position during the operations of inserting several transverse screws.

Another disadvantage is that the limb must be surgically opened along the fracture site, and the opening must be quite long (and also wide) to permit the surgeon to place the plate and the various transverse screws along the length of the plate about the fracture site.

In an attempt to overcome these disadvantages of the plate and screw method, previous workers have used intramedullary rods (hereinafter, "IM rods" or "nails") to repair fractures.

The IM rod is better than an external plate because it can be inserted into the bone from one end, avoiding the long surgical incision required for placement of the plates. For example, the upper end of the femur is accessible through a small incision in the hip. A hole can be drilled through the upper end of the femur into the endosteal canal, the inner space that is surrounded by hard bone tissue (cortical bone), and the IM rod can then be inserted into the endosteal canal.

With a long steel rod running through it, the bone is well fixed against bending. Also, if the outer diameter of the IM rod is close to the inner diameter of the endosteal canal at the location of the break, the fractured ends are automatically aligned with each other so that the fractured edges will mate properly for healing.

However, if the IM rod has a diameter which is close to the inner diameter of the endosteal canal it may be quite difficult to insert because the endosteal canal is irregular in shape. Ideally, the endosteal canal in the region of the break would be a uniform tube like the interior of a pipe (or in the case of the femur, which is bowed, like the interior of a hoop); then the rod could be inserted if its diameter were only slightly less than the inner diameter of the bone.

It will be clear on reflection that even in this ideal case the bone segments will not be held against relative rotation about the long axis of the bone. Unless the IM rod is firmly held to the bone in some manner, the broken bone segments will easily rotate about the rod, even though the play between the rod and the interior of the bone is limited to only a millimeter or so. If the IM rod is fixed in play by friction, that is, with slight interference fit, then the rod will be quite difficult to insert.

Moreover, the endosteal canal is not geometrically perfect. The only IM rod shapes which are capable of being inserted without undue force are those which are incapable of maintaining a small clearance over large areas. When the rod is inserted it will make contact at a very few points, while most of its surface will be suspended relatively far from the inside of the bone. Braced only at three or four points, it will be able to wobble about inside, and the longitudinal alignment and the fractured-end alignment is likely to be lost. Furthermore, it will not be possible to prevent rotational displacement.

Even an optimally-shaped rigid IM rod will provide poor control of bending and/or end mating, and will provide rotational control only to the extent that it is forced into place. If the IM rod is jammed in, then there will be some frictional force against rotation. However, since the inside of a bone is wet and slippery, the amount of anti-rotation force will be considerably less than the force pressing the bone against the rod. To achieve a large anti-rotation force, the rod must be jammed into the endosteal canal quite hard, causing large local forces. Bone damage is likely to result.

The problems involved with IM rod design are noted in U.S. Pat. No. 4,784,127 to Mattheck et al, who explain that in some IM rods "the nail . . . comes into contact with the bone wall only in very limited longitudinal regions, i.e. is lacking as regards transverse clamping" while in others a "high rate of cracks and tearing has been found" (column 1, lines 18–24).

The prior art illustrates repeated attempts to achieve an IM rod which: (1) fits close to the interior of the endosteal canal over a large area, so the bone will be held against longitudinal wobble; (2) provides a strong antirotation force, so that the bone cannot twist about the rod; and (3) avoids large forces on only a few small areas, which can damage the bone, and instead distributes the stress over a large area. However, the known IM rods have not adequately achieved all of these features.

Kyle et al, in U.S. Pat. No. 5,034,013, disclose a flexible IM rod which is stated to be an improvement over the those which are "too rigid to follow the usually imperfect intramedullary bone canal" and which cause "chipping" (column 1, lines 27–31). The flexibility is achieved with a deep longitudinal groove and shallower flutes. Of course, what is gained in flexibility is lost in stiffness; Kyle et al have not solved problems (1) and (2) above.

A different approach is disclosed by Engelhardt et al in U.S. Pat. No. 4,805,607, showing a two-part nail which is curved to follow the curve of the femur. Engelhardt uses fluting also, but to form flanges 26 (FIG. 6), the leading edges of which include sharp points 30. Engelhardt states that "the flanges 26 digging into the bone reduce the ability of the nail to undesirably rotate inside the bone" (column 4, lines 14–16).

The flutes themselves are not actually able to "dig into" the bone, as Engelhardt asserts, because they are smooth on their outer surfaces and can only slide along the inside of the endosteal canal. The leading edges of the flanges, with the "sharp points", can actually cut, but these points are ill-adapted to their task because their sharp edges are radial to the rod axis, as seen in FIG. 5. As a consequence the edges will not remove any bone tissue but instead will act as wedges, tending to split the bone apart like a wedge in a tree stump.

Hannon, in U.S. Pat. No. 5,116,335, discloses an IM nail for internal fixation of a long bone which aims to improve torsional rigidity and avoid the weakness of two-part nails such as that of Engelhardt. Hannon's nail is based on expansion into the cancellous tissue at either end of the long bone, where the endosteal canal increases in diameter.

The Hannon nail has a rigid center rod 18 with longitudinal slots and three flexible outer rods 20 which slide in the slots 22. The rods have "retention sections" which penetrate the cancellous tissue at the ends of the bone. The two retention sections of each rod are radially thicker than the middle portion, so that when the rod is inserted in its slot in the center rod the ends protrude radially at the ends.

Because of this shape, the three outer rods 20 must be inserted into the bone before the center rod 18 is inserted; otherwise, there would be no room for the higher distal ends of the rods to pass the central canal. After the outer rods are fully inserted past the fracture site, the center rod is slid in, which forces the distal sharpened points 50 with "arrow-point" tips 48 (column 5, line 33; FIG. 4) to penetrate into the cancellous tissue (column 5, line 27). Hannon sets this out in discussing the insertion procedure starting at column 6, line 33.

Any increased anti-rotation resistance of the Hannon rod derives from the elevated end points 48 that are driven into the cancellous tissue; the upper surfaces in the middle portion are smooth and can exert no meaningful force on the bone directly at the fracture site. All of the anti-rotation force is applied at the ends of the bone, far from a central fracture, and is not spread out over the length of the bone. There is no fixation at the fracture site. In this, the Hannon nail is no advance over the external plate.

The existing IM rods do not provide firm fixation of long bone segments in bending, lateral position, and rotation, with evenly distributed force.

SUMMARY OF THE INVENTION

Accordingly, the present invention has an object, among others, to overcome deficiencies in the prior art such as noted above.

The invention relates to an intramedullary ("IM") rod to be inserted into a long bone from one end for alignment following a fracture. The operation preparatory to insertion of the rod, including drilling a hole in one end of the bone, is conventional. The rigid rod includes longitudinal slots in which flexible splines slide. Unlike prior-art IM rods, the present invention has transverse cutting teeth on the splines, which automatically provide a firm but low-stress fit between the bone and the rod.

The rod is inserted into the bone from one end. While the bone fragments are correctly positioned both longitudinally and rotationally, the cutting splines are inserted into the slots and forced along. The splines are high enough that they interfere with the inside of the endosteal canal; however, their cutting teeth cut shallow grooves into the bone, which are exactly fitted to the splines because the splines cut them.

Each of the transverse cutting teeth of a spline is set very slightly higher than the tooth cutting in front of it. As the spline advances, each cutting tooth follows in the groove that the leading tooth has already cut. The teeth are ramped, lower in front and higher in back, so that a leading tooth is set very slightly lower than the tooth which follows. The trailing tooth has merely to shave a paper-thin layer from the bottom of the groove that the slightly-lower leading tooth has already cut. Because the cut is shallow, the force exerted by each cutting tooth is small and there is little chance of fracture. The shavings are accumulated in the spaces between the teeth and there is likewise no risk of excessive force from jamming.

The spines, when fully inserted, are firmly held along their entire lengths in two directions. Radially, they are held between the slots in the central rod and the bottoms of the grooves they have cut into the bone; circumferentially, the teeth are also held firmly within the slots and grooves. Because the teeth have cut the bone groove there is no play whatsoever between the splines and the bone.

The splines, though non-hinged and unitary (as seen in FIGS. 1 and 4), are preferably somewhat flexible in the radial direction to follow the curve of the rod, which may be the conventional curvature imparted to IM nails or rods. As noted above, the femur is bowed; the tibia also includes a curved interior especially at its upper end. This flexibility also insures that the splines exert radial force evenly along their lengths, and because of it the splines will bottom everywhere in the slots.

The only play between the bone and the rod is the circumferential play between the spline and the rod slot. Since this clearance is measured in thousandths of an inch with ordinary machining tolerances, it is clear that the rotational play of the bone is so small as to be negligible.

An advantage of the present invention is that the splines automatically align the fractured ends of the bone segments. The cross-sectional shape of course, is the same just on either side of a break, and the spline teeth increase their height only incrementally. Therefore, unless the two segments are widely separated the ends will be automatically aligned. If the fractured ends are separated, any misalignment can be corrected by merely pushing the two ends together and then advancing the splines.

The rod is easily inserted, because there is no need for it to closely match the interior shape of the endosteal canal; the fit of the rod to the endosteal canal need be only approximate. The splines take up the clearance and bridge across any gap between the rod surface and the bone surface.

The splines may include some structure to lock them into the slots; for example, a "T" head on the base of the spline and a mating shape at the bottom of the slot. This can make the rod/splines assembly easier to handle. The cutting teeth are sharp, and a waving spline can be inconvenient. The T-shaped spline bottom also will prevent buckling of the spline in regions of the endosteal canal where the bone may be farther from the rod and the teeth do not cut any groove.

In the preferred embodiment of the present invention just two splines are used, located diametrically opposite each other across the rod and each lying in the plane of curvature (if any) of the rod. The T-head on the base of the spline can optionally be kerfed (notched at intervals) so that the spline is flexible in two bending directions instead of one. This might be useful when more than two splines are used; with more than two splines and a curved rod, one of the splines will need to bend sideways as well as radially.

As noted above, the force exerted on the bone by any one tooth is not dangerously large. However, the force exerted by all the teeth at once shaving the hard bone is substantial, and the splines may need to be tapped in the distal direction. A clamp, such as a locking pliers, may be used to grasp the spline close to the slot insertion point at the proximal end of the IM rod, and the clamp tapped downward. Preferably, the spline includes indentations, notches, holes, or depressions adapted to be grasped by the locking pliers.

The present invention also contemplates the use of sleeves slid over the length of a spline as it extends from the proximal end of the rod during insertion. Such a sleeve allows the spline to be hammered on the non-inserted end without buckling, and permits the hammering force to be transmitted along the spline to the cutting teeth.

The same indentations or holes useful for inserting the splines can also be used to remove the splines, preparatory to removing the rod. Removal will be necessary in case of infection induced during insertion or later problems, sometimes the rod is removed once the fracture has healed. The proximal end of the rod preferably includes a threaded hole or slot to engage a removal tool.

The slots preferably diverge radially (away from each other) at the distal end. This forces the flexible splines to diverge there and penetrate into the cancellous tissue at the enlarged end of the bone. The splines may include pointed ends to help them penetrate into the tissue. Such pointed ends are completely distinct in function from the cutting teeth along the spline, which cut the hard cortical bone; however, the leading distal tooth can be part of the penetrating point.

The proximal end of the slotted rod may include a flange to prevent the rod from migrating too far into the bone (in the distal direction).

If the rod is inserted into marrow, the slots may be made shallower at the inserted or distal end so that the splines will diverge away from the rod into the softer marrow.

When the spline or splines have been driven into the slots, they provide a very firm anchoring of the IM rod because there is no lateral gap and the rod is prevented from rotating within the bone. A curved rod can be fixed in place just as well as can a straight rod.

To provide for later retraction of the IM rod and/or to permit reuse of the cutting splines, blank splines may be substituted for the cutting splines after the grooves have been cut into the bone. Since they have no recesses, such blank splines can be retracted more easily. Furthermore, they are less likely to be anchored by cortical growth.

BRIEF DESCRIPTION OF THE DRAWING

The above and other objects and the nature and advantages of the present invention will become more apparent from the following detailed description of an embodiment taken in conjunction with drawings, wherein:

FIG. 3 is an elevational, end view of a spline.

FIG. 4 is a partial perspective view of the spline and rod.

FIG. 5 is a partial cut-away perspective view of a proximal end of the invention.

FIG. 6 is a cross-sectional view of the present invention in use.

FIG. 7A is a perspective view showing insertion of the spline.

FIG. 7B is a perspective view showing a detail of FIG. 7A.

FIG. 8 is similar to FIG. 7A but showing alternate insertion.

FIG. 9 shows a blank spline.

DETAILED DESCRIPTION OF THE PREFERRED EMBODIMENT

Figure 1:
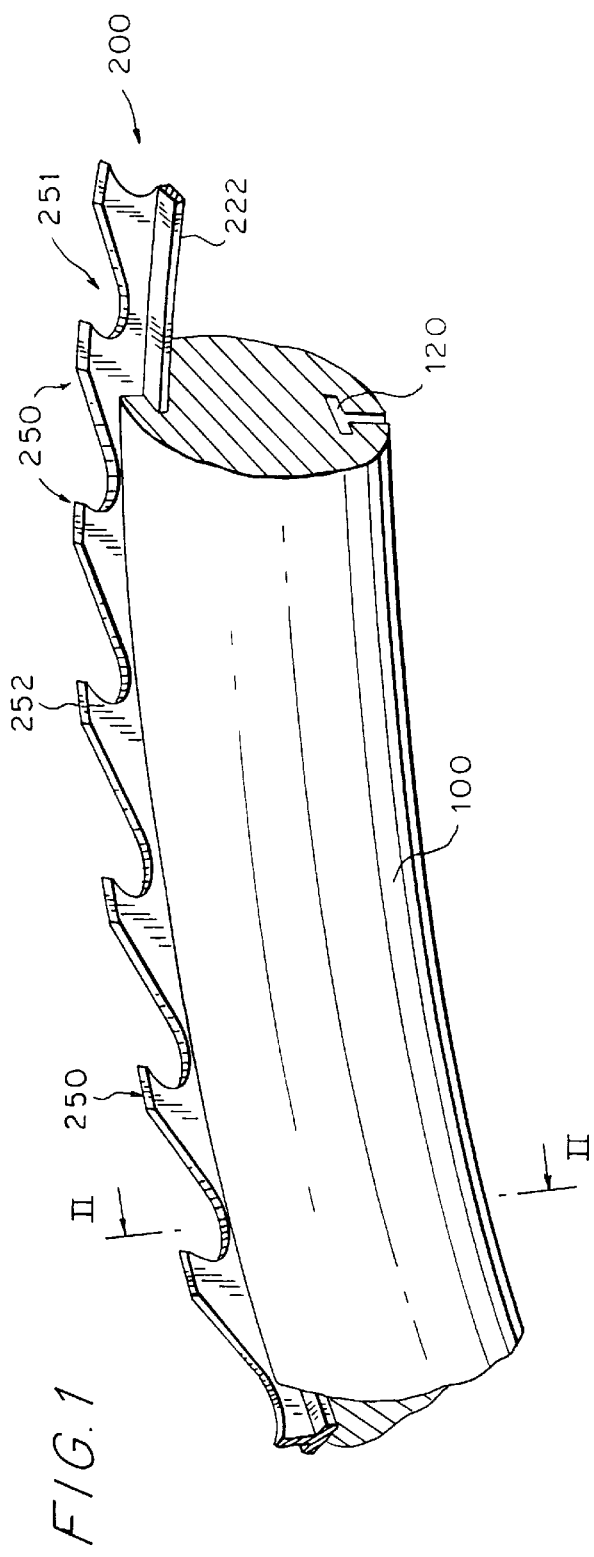
FIG. 1 is a perspective view of a broken-away piece of the present invention.

FIG. 1 shows an intermediate portion of the present invention, an intramedullary (IM) rod or IM nail, to be inserted into the endosteal canal of a fractured long bone (humerus, clavicle, etc.; especially the femur or tibia). There are two major parts: a rod 100 and a spline 200. Only one spline is shown in FIG. 1 for clarity; in use the unoccupied slot 120 would also contain a spline 200. The slots and splines preferably number two as shown, but any number can be used in the present invention.

The rod 100 can be unitary with machined (or forged) slots, or built up in sections equal in number to the number of splines and slots. The preferred material for splines 200 is stainless steel, and the preferred materials for the rod 100 are stainless steel and titanium.

The splines 200 slide axially within the slots 120. The slots 120 may be of any shape but preferably are either simple rectangles or else are T-shaped as shown in the drawing, including a T-base 122 (best seen in FIG. 2, a cross section on lines II—II of FIG. 1). The T-base 122 holds a mating T-base 222 of the spline 200 (best seen in FIG. 3). The apparatus may include lubricant and/or a strip or strips of high density polyethylene, etc. (not shown) to aid in sliding of the spline 200 into the slots 120.

The spline 200 includes a plurality of cutting teeth 250 on its outer surface. The teeth extend out from the surface of the rod 100 when the spline 200 is in the slot 120. Between the cutting teeth 250 are recesses 251, which are sufficiently deep to hold bone material shaved by the teeth 250, as discussed below, and also deep enough that the spline 200 as a whole is flexible to follow the curve of the rod 100. The rod 100, which is inserted into a fractured long bone, may be slightly curved as shown in the drawing to better slide into the endosteal canal of the curved bone. For use in straight bones the rod 100 is preferably straight. The T-bases 122 and 222 keep the flexible spline 200 from buckling when it is subjected to compression force, as discussed below.

Figure 2:
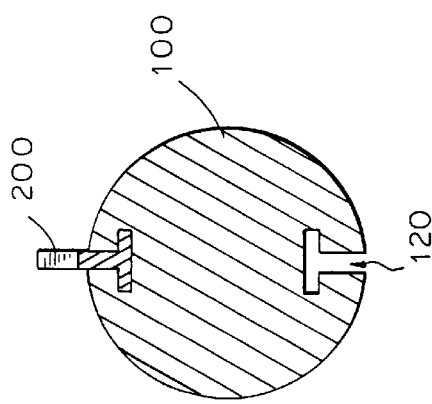
FIG. 2 is a cross-sectional view along line II—II of FIG. 1.

FIG. 2 shows a section on lines II—II of FIG. 1.

FIG. 3 is an end view of a spline 200 at the distal end. Here, "distal" refers to the end farthest from the point of insertion into the bone. FIG. 3 shows an optional beveled point 201, the T-base 222, and a plurality of the cutting edge 250. The edges 250, appearing as close-set lines in FIG. 3, are each preferably set at a different height above the spline base 210. Each is offset from the adjacent tooth by an increment of the radial height, that is, the cutting teeth 250 are staggered, with height differentials. The tooth height is taken radially, along a line perpendicular to the axis of the rod 100. The cutting edge height increases from the distal end of the spline 200 toward the proximal end. In FIG. 1, the teeth are higher on the left side.

The cutting teeth 250 are preferably inclined in the cutting direction, i.e., toward the right in FIG. 1, as illustrated. The teeth 250 are also shown in FIG. 4.

Because of the increasing offset, the spline will gradually cut a groove into the bone as it moves in the distal direction along the slot 120. Each tooth will cut off a thin shaving, like shaving from a wood-working plane; no excessive force will be exerted on the bone.

FIG. 6 shows the spline 200 slidably engaged with the slot 120 at a point where the spline 200 has cut a groove G into a bone B. The groove is exactly the shape of the teeth and there is very little play between the bone B and the spline 200. The annular gap between the outer, preferably cylindrical surface of the rod 100 and the inside of the endosteal canal (the lower surface of the bone B in FIG. 6) is bridged by the spline 200. The spline bottom 210 (lower surface of the spline 200) is pressed firmly against the bottom of the slot 120.

Preferably, each cutting tooth 250 includes a tooth top surface 252 which is parallel to the spline bottom surface 210. This top surface 252 rests against the bottom of the bone groove G and resists any tendency for the cutting edge, located at the distal end of the flat surface, to dig into the bone B and "gouge" it. The top surfaces 252 form a sort of staircase. Preferably, the cutting edges of the teeth 250 are formed by the top surfaces 252 and the recesses 251; the teeth 250 may be sharpened by grinding the recess 251 where it meets the top surface 252. The top surfaces 252 may optionally be hardened by nitriding, hard chrome plating, or other conventional means.

The top surfaces 252 are preferably flat, but may be cylindrical or any other shape. They may also be alternatingly set to opposing angles, like the teeth of a rip saw; in this case the bottom of the bone groove G will be peaked like a roof instead of flat.

The radial height of the leading (most distal) tooth 250 is preferably only slightly greater in radial height than the outer surface of the rod 100. The cutting teeth 250 increase steadily toward the proximal end, rising to the radial height where a groove G will be formed but remaining radially short enough that the groove G will not weaken the bone B.

The height increments of the teeth 250 may describe various functions. For one, the radial height increments may be equal as in a staircase. Alternatively, the increments may decrease with longitudinal distance from the distal end, so that the leading cutting edges remove proportionally more of the bone material; and indeed the cutting teeth may all be the same height past a certain distance from the distal end, and in this case those past that point need not be sharpened. This arrangement will make the force needed to advance the splines along the slots more nearly constant, in contrast to the even-staircase design in which the force increases steadily as the splines advance. The force increases as one tooth after another begins to cut. The amount of cutting delegated to the proximal teeth is limited by the storage capacity of the recesses 251, which must have enough volume to hold the bone shavings cut off by the teeth 250 or jamming will result.

The IM rod of the present invention will usually be left in place until the bone is healed, unless some complication requires it to be removed earlier. Until the rod and splines have been in place for a couple of months, there will be little bone growth extending hard bone material into the recesses 251 between the cutting teeth 250. These interstices will be free of bone and the splines will be relatively easy to withdraw. However, if the splines 200 and rod 100 need to be removed after having been implanted for about three months, then the splines may be more difficult to withdraw because hard bone will have grown into the recesses 251.

One way to make removal easier is to design the teeth 250 to cut on the way out as well as on the way in. FIG. 4 shows an embodiment in which the rear (proximal end) of each tooth includes sharpened edges on the rear of the top surface 252 and the rear sides of the tooth as well, so that the rear end of the tooth 250 presents two parallel sharp edges on the sides and one sharp edge perpendicular to the side edges. The sharp rear edges are easily formed by grinding the rear of each tooth 250 to a flat rear surface 254. Preferably, the angle between the rear surface 254 and the top surface 251 is about 90 degrees, or the rear surface is slightly inclined with the rear edge being undercut slightly by the recess 251 as shown in FIG. 4. In FIG. 4 the front surface 253 is shown as being more acutely angled for increased cutting power.

The rear surface may also be angled about a line radial to the rod 100 when the spline is in the slot 120, or the rear side of the teeth may be hollow-ground to provide a more acute backward cutting edge (not shown).

FIG. 4 also shows another feature of the present invention which is intended to facilitate removal, a narrow gap between the teeth 250 and the placement of the greater volume of the recess 251 inside the rod 100. This structure leaves only a narrow gap into which bone can grow, and therefore makes it easier to break off any bone which has grown into the inter-tooth gap. The retraction force does not depend on the amount of bone which is inside the recess 251, only the area of ingrown bone which must be sheared.

Alternatively, the gaps between the teeth 250 can be narrowed to a mere slot (not shown in FIG. 4) with the front surface 253 and the rear surface 254 set essentially parallel. With this structure the angled narrow slot provides a guide passage for the bone shaving cut by the front edge to pass into the recess, which can be entirely disposed within the slot 120. The side area of the slot, top and sides, is minimal for easy retraction of the spline 200 even after long implantation.

Another feature (not shown) is to angle one or both sides of the teeth 259 so that the teeth 250 are slightly wedge-shaped as seen in a section plane tangent to the rod 100. If the wedge is narrower at the front or distal end, then when the spline 200 is withdrawn the sides of the teeth will tend to separate from the bone in tension rather than purely in shear. Similarly, the tooth top surface 252 can be angled very slightly. Slight angling of the top and sides of the teeth 250 will not adversely affect the lateral hold of the spline 250 within the bone groove G.

Still another approach to withdrawal of the splines is shown in FIG. 9, discussed below.

FIG. 4 also shows indentations 260, used for grasping the spline 200 with locking pliers (not shown in FIG. 4). In addition, FIG. 4 shows kerfs 221 which may be provided to increase the transverse flexibility of the spline 200, should that be required, and also shows how the recess 251 comes quite close to the T-base 222 to provide spline flexibility in the radial direction, for dual splines traversing the rod 100 along lines lying in a plane bisecting the rod 100. Like the indentations 260, the kerfs 221 may also provide a grasping point for inserting or removing the spline 200.

A rim or flange 101 may be provided on the proximal end of the rod 100, as shown in FIG. 4, to prevent the rod 100 from moving too far into the bone B.

FIG. 3 and FIG. 5 show an optional feature intended to force the splines into the cancellous tissue at the distal end of the bone. In FIG. 3, the distal end of the spline is shown to include a beveled point 201. In FIG. 5, the distal end of the slot 120 includes an upward or outward rise 121 of the slot T-base 122, so that it clears the surface of the rod 100 before it reaches the distal end. This rise forces the splines to angle outward when they reach the distal end of the rod 100, so that they engage the cancellous tissue by penetrating it.

FIG. 7A shows the insertion of the spline 200 into the end of a long bone B using a locking pliers 700 and a hammer 750. The rod 100 has been inserted first; the proximal end protrudes from the bone B for illustration, though in actual use the proximal end may be disposed inside the bone B. The jaws 720 of the locking pliers 700 preferably include one or more protrusions 760, shown in FIG. 7B, which mate with the indentations 260 shown in FIG. 4. The protrusions 760 preferably engage a pair of opposing indentations 260 on opposite sides of the spline 200 and are held firmly within them by the jaw-closing force of the locking plier mechanism, which is conventional. With the spline 200 so firmly held, a hammer 750 is used to apply strong inserting force.

The indentations 260 and protrusions 760 may be any shape, may be reversed in convexity, and may include steps to resist the protrusions 760 being knocked out by hammer blows; in general, the present invention includes any adaptation to increase the available force beyond that due solely to friction when the spline is gripped. As noted above, the kerfs 221 of the spline T-base 222 may also be used to grasp the splines 200.

The splines 200 may alternatively be provided with holes, rather than indentations, into which the tip of a lever can be inserted to pry the spline in the distal direction. A fulcrum may be provided on the proximal end of the rod 100 for prying to exert a force aiding insertion or withdrawal of the spline 200 (not shown). The kerfs 221 also may be used as leverage points, and pried with a slot-tip screwdriver or the equivalent, thus augmenting the force applied on the indentations 260.

FIG. 8 shows an alternative to FIG. 7A. FIG. 7A shows the spline 200 grasped quite close to the proximal end of the rod 100, which prevents the hammer blows from buckling the spline 200. The alternative structure of FIG. 8 is a sleeve 800 which slides over the length of spline 200 protruding from the proximal end of the rod 100. The sleeve 800 includes an internal T-aperture to accept the T-shaped spline 200. The sleeve 800, struck on the end with the hammer 750, prevents the non-inserted length of the spline 200 from buckling. An assortment of sleeves 800, of various lengths, may be provided.

FIG. 8 also shows a threaded hole 170 in the proximal end of the rod 100, which provides an anchoring point for retracting the rod 100 from the bone B.

FIG. 9, mentioned above in relation to retraction of the splines, illustrates a blank spline 300. The blank spline 300 is like the cutting spline 200, having a T-base 322 and, optionally, a point 301 like the cutting spline 200, but it lacks cutting teeth 250. Instead it has a ramp 350 with a smooth upper surface 352. The ramp may be stepped to match the heights of the cutting spline 200, but may more simply be made as a smooth ramp following the curve circumscribing the teeth 250.

After the bone groove G (FIG. 6) has been cut by the cutting spline 200, the cutting spline is withdrawn and the blank spline 300 is put in its place in the slot 120. Since the blank spline 300 has no interstices, bone growth cannot embed the blank spline 300 so firmly as the cutting spline 200, and removal of the rod 100 is far easier. At the same time, there is no loss of strength (in fact the strength is slightly greater) and there is less chance of pain from sharp edges. An added benefit is that the blank splines are less expensive than the cutting splines, which are re-useable and can be re-sharpened using conventional devices.

It is clear from the above description that the present invention eliminates the large local forces which can cause damage to the bones, and it firmly holds the bone segments in their proper positions. It will also be appreciated that the present invention causes little disruption to the bone tissue in comparison to prior-art IM rods, because the volume occupied by the present invention is minimal.

The present invention has the unique advantage that rotational fixation is obtained as soon as the cutting teeth 250 engage the bone on the distal side of the fracture, providing immediate rotational control. Once the splines 200 are moved past the fracture and are emplaced in the groove G on either side of the fracture line, the splines act as keys to resist relative rotation of the broken segments at the fracture line, not far away from it as in the prior art.

With modifications, the present invention can be used to remove cement left in a bone, e.g., cement left after a failed hip implant is removed. If the rod 100 is made small enough to pass through the hole left by the stem of the implant, the splines 200, especially if made radially high, can cut deep grooves into the cement, allowing it to be broken up.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. An intramedullary apparatus for aligning a long bone (B) fractured into segments, the apparatus comprising:
   a rod (100) having at least one longitudinal slot (120), the slot having a slot bottom; and
   a non-hinged cutting spline (200) slidable in the slot, the cutting spline including a spline bottom slidable along a respective one slot bottom and a spline upper surface opposite the spline bottom, the spline upper surface including a plurality of cutting teeth (250) for cutting a groove (G) into the bone when the cutting spline is moved along the slot and the rod is in place in the intramedullary region of the bone;
   whereby the bone segments are held against bending, rotation, and lateral displacement when the rod is inserted into the bone and the cutting spline is slid along the slot.

2. The apparatus according to claim 1, wherein the teeth include cutting edges substantially transverse to a longitudinal extension of the slot.

3. The apparatus according to claim 4, wherein at least some of the cutting edges are staggered at various different values of the radial height.

4. The apparatus according to claim 2, wherein the spline upper surface includes a plurality of tooth top surfaces (252) each disposed at a respective radial height associated with a respective one of the teeth, and wherein the top surfaces comprise the cutting edges.

5. The apparatus according to claim 1, comprising recesses (251) disposed adjacent the cutting teeth, whereby bone shavings may be stored in the recesses to prevent jamming.

6. The apparatus according to claim 1, wherein the rod is rigid and the cutting spline is unitary and somewhat flexible.

7. The apparatus according to claim 1, wherein the rod comprises a plurality of longitudinal slots (120) angularly spaced apart and the apparatus includes a corresponding number of respective cutting splines.

8. The apparatus according to claim 7, wherein the plurality of slots numbers two.

9. The apparatus according to claim 8, wherein the rod is curved and the slots are disposed on an inside and on an outside of the curve of the rod, whereby a curved center line of the rod and the two slots are substantially coplanar.

10. The apparatus according to claim 1, wherein the slot and the cutting spline are matingly T-shaped.

11. The apparatus according to claim 1, wherein the slot comprises an outward rise (121) at a distal end of the rod and the cutting spline includes a point (201).

12. The apparatus according to claim 1, wherein the spline includes an indentation or hole for gripping.

13. A method for aligning a long bone (B) fractured into segments, the bone having an endosteal canal of an intramedullary region of the bone, the method comprising the steps of:

providing a rod (100) having at least one longitudinal slot (120), the slot having a slot bottom;

providing a non-hinged cutting spline (200) slidable in a respective one slot, the cutting spline including a spline bottom slidable along the slot bottom and a spline upper surface opposite the spline bottom, and the spline upper surface including a plurality of cutting teeth (250);

inserting the rod into the endosteal canal; and cutting a groove (G) into the bone by advancing the cutting spline along the slot while the rod is in place in the intramedullary region of the bone, whereby the bone segments are held against bending, rotation, and lateral displacement when the rod is inserted into the bone and the cutting spline is slid along the slot.

14. The method according to claim 13, comprising the steps of:

removing the cutting spline;

providing a blank spline (300), the blank spline being similar in shape to the cutting spline but lacking the cutting teeth; and inserting the blank spline in the slot in place of the retracted cutting spline.

15. A kit for aligning a long bone fractured into segments, comprising:

an intramedullary apparatus in accordance with claim 1; and a blank spline of the same dimensions as said cutting spline but having no cutting teeth.

16. A kit for aligning a long bone fractured into segments, comprising:

an intramedullary apparatus in accordance with claim 12; and means for gripping said cutting spline at said indentation or hole.

17. A kit for aligning a long bone fractured into segments, comprising:

an intramedullary apparatus in accordance with claim 1; and a hammer.

18. A kit for aligning a long bone fractured into segments, comprising:

an intramedullary apparatus in accordance with claim 1; and a plurality of spline sleeves having an internal slot corresponding in shape to the cross-section of said cutting spline and dimensioned to fit longitudinally over said spline, each of said plurality of spline sleeve having a different longitudinal length.

19. The apparatus according to claim 1, wherein the teeth are alternatingly set to opposing angles.

* * * * *